United States Patent
Han et al.

(10) Patent No.: US 6,316,695 B1
(45) Date of Patent: Nov. 13, 2001

(54) **ISOPENTENYL DIPHOSPHATE ISOMERASE FROM *HEVEA BRASILIENSIS* AND RUBBER PRODUCING METHOD USING THE SAME**

(75) Inventors: Kyung-Han Han; Hun-Seung Kang, both of Kwangju; Soo-Kyung Oh, Kyunggi-do; Dong-Ho Shin; Jae-Mo Yang, both of Kwangju, all of (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 0 days.

(21) Appl. No.: 09/296,754

(22) Filed: Apr. 22, 1999

(51) Int. Cl.$^7$ .............................. C12N 15/82; C12N 5/10; C12N 1/15; C12N 15/29; A01H 5/00

(52) U.S. Cl. .......................... 800/278; 800/298; 800/295; 435/166; 435/183; 435/468; 435/471; 435/483; 435/484; 435/488; 435/814; 435/320.1; 435/254.1; 435/252.3; 435/252.33; 536/23.2; 536/24.1; 536/23.6

(58) Field of Search ................................. 536/23.2, 24.1, 536/23.6; 435/166, 468, 488, 183, 814, 483, 471, 484, 320.1, 254.1, 252.3, 252.33; 800/278, 298, 295

(56) References Cited

U.S. PATENT DOCUMENTS 4,638,028 * 1/1991 Lui et al. ............................... 524/387
4,983,729 * 1/1991 Sikora ..................................... 536/28

OTHER PUBLICATIONS

Oh et al. Accession No. AF111842 Deposited, Dec. 1998.*
Jung et al. Accession No. AF031079, Deposited, Oct. 1997.*
Attanyaka et al. Plant Molecular Biology 16: 1079–1081, 1991.*
Blanc et al. Accession No. X82627, Deposited, Nov. 1994.*
Blanc V., et al., "Nucleotide Sequence of Clarkia breweri cDNA Cloone of Ipi1, a Gene Encoding Isopentenyl Pyrophosphate Isomerase" *Plant Physiol*, vol. 108, pp. 855–856, 1995.
Tangpakdee, J., et al. "Isopentenyl Diphosphate isomerase and Prenyl Transferase Activities in Bottom Fraction and C–Serum from Hevea Latex" *Phytochemistry*, vol. 45, No. 2, pp. 2661–267, 1997.
Cornish, K., "The separate roles of plant cis and trans prenyl transferases in cis–1,4–polyisoprene biosynthesis" *Biochem. Journal*, vol. 116, pp. 267–271, 1993.

Kajiwara, S., et at. "Expression of an exogenous isopentenyl diphosphate isomerase gene enhances isoprenoid biosynthesis in *Escherichia coli*" *Biochem. Journal*, vol. 324, pp. 421–426, 1997.

Valdivia, A., et al. "Purification and characterization of two isoforms of isopentenyl–diphosphate isomerase from elicitor–treated Cinchona robusta cells." *EJB* 1997 pp. 470–474, 1997.

Valdivia, A., et al. Elicitor–mediated induction of anthraquinone biosynthesis and regulation of isopentenyl diphosphate isomerase and farnesyl diphosphate synthase activities in cell suspension cultures of Cinchona robusta How. *Planta* vol. 203, pp. 155–161, 1997.

Campbel, M., et al., "Analysis of the isopentenyl diphosphate isomerase gene family from Arabidopsis" Plant Molecular Biology, 36:323–328, 1997.

* cited by examiner

Primary Examiner—David T. Fox
Assistant Examiner—Medina A. Ibrahim
(74) Attorney, Agent, or Firm—Mathews, Collins, Shepherd & Gould, P.A.

(57) ABSTRACT

The present invention cloned a cDNA clone encoding isopentenyl diphosphate (hereafter "IPP") isomerase (EC 5.3.3.2) from a cDNA library of *Hevea brasiliensis* latex. The clone has a continuous open reading frame encoding a peptide of 234 amino acids with a predicted molecular mass of 26.7 kDa. The deduced protein is acidic with an isoelectric point of 4.7 and shows high sequence identity with other IPP isomerases. The recombinant protein expressed in *Escherichia coli* showed IPP isomerase activity. In vitro rubber biosynthesis assays using washed rubber particle (WRP) deprived of initiating allylic diphosphates were performed with the addition of IPP isomerase in the reaction mixture. Results revealed that the recombinant IPP isomerase is catalytically active in catalyzing the conversion of IPP to DMAPP, a key activation step of the basic five-carbon isoprene unit in rubber biosynthesis. Southern analysis indicated that the IPP isomerase is encoded by two genes in Hevea rubber tree. In Northern blot analysis, two different sizes of transcripts (1.2 and 0.6 kb) were detected from leaf tissues while only one hybridizing band (1.0 kb) was detected from latex. Analyses of RNA extracted from extruded latex and leaf tissues of the trees wounded with nails showed that wounding did not change the transcript level of IPP isomerase.

18 Claims, 3 Drawing Sheets

SEQUENCE LISTING

```
<160> NUMBER OF SEQ ID NOS: 2

<210> SEQ ID NO 1
<211> LENGTH: 1288
<212> TYPE: DNA
<213> ORGANISM: IPIHb (IPP isomerase from Hevea brasiliensis)
<220> FEATURE:
<221> NAME/KEY: CDS
<222> LOCATION: (209)..(910)

<400> SEQUENCE: 1
caccactcgc cttctaaatg cccacgccac caccagactc tcgtcctcgc ttccctcctc        60
tgcttctcct cgttattctt actttctctc tacccaattt gcctctcctt ctctcattca       120
attccctcta actcttaaac cttcgtctac ctcttcgttc tctagggtat tttcgtcttc       180
tccatctgca atcaccgcta cttccacc     atg ggt gag gct cca gat gtc ggc      232
                                  Met Gly Glu Ala Pro Asp Val Gly
                                   1               5 atg gat gct gtc cag aaa cgc ctc atg ttc gac gat gaa tgc att tta         280
Met Asp Ala Val Gln Lys Arg Leu Met Phe Asp Asp Glu Cys Ile Leu
     10                  15                  20
```

-continued

```
gta gat gag aac gat ggt gtt gtt ggt cat gct tcc aaa tat aat tgt          328
Val Asp Glu Asn Asp Gly Val Val Gly His Ala Ser Lys Tyr Asn Cys
 25              30                  35                  40 cat ttg tgg gaa aat att ttg aag ggg aac gca tta cat aga gct ttt          376
His Leu Trp Glu Asn Ile Leu Lys Gly Asn Ala Leu His Arg Ala Phe
                 45                  50                  55 agc gta ttt ctc ttc aac tca aaa tat gag cta ctc ctt cag caa cgc          424
Ser Val Phe Leu Phe Asn Ser Lys Tyr Glu Leu Leu Leu Gln Gln Arg
             60                  65                  70 tct ggg aca aag gtg aca ttc ccg ctt gta tgg aca aac act tgc tgt          472
Ser Gly Thr Lys Val Thr Phe Pro Leu Val Trp Thr Asn Thr Cys Cys
         75                  80                  85 agt cat cct ctg tac cgt gaa tct gag ctt att gat gag gat gct ctt          520
Ser His Pro Leu Tyr Arg Glu Ser Glu Leu Ile Asp Glu Asp Ala Leu
     90                  95                 100 ggt gtg aga aat gct gca caa agg aag ctt ttc gat gag ctt ggt atc          568
Gly Val Arg Asn Ala Ala Gln Arg Lys Leu Phe Asp Glu Leu Gly Ile
105                 110                 115                 120 cct gct gaa gat gtt cca gtt gat cag ttt act cca cta gga cgt ata          616
Pro Ala Glu Asp Val Pro Val Asp Gln Phe Thr Pro Leu Gly Arg Ile
                125                 130                 135 cta tat aag gcg tcc tcc gat gga aag tgg gga gag cat gaa ctt gat          664
Leu Tyr Lys Ala Ser Ser Asp Gly Lys Trp Gly Glu His Glu Leu Asp
            140                 145                 150 tat ctg ctc ttt ata gtc cgt gat gtt aat gta aat cca aac cct gat          712
Tyr Leu Leu Phe Ile Val Arg Asp Val Asn Val Asn Pro Asn Pro Asp
        155                 160                 165 gag gta gct gat gta aag tat gtt aac cgg gat cag ttg aag gag ctc          760
Glu Val Ala Asp Val Lys Tyr Val Asn Arg Asp Gln Leu Lys Glu Leu
170                 175                 180 ttg agg aag gcg gat tct ggc gag gaa ggt ata aat ttg tca cct tgg          808
Leu Arg Lys Ala Asp Ser Gly Glu Glu Gly Ile Asn Leu Ser Pro Trp
185                 190                 195                 200 ttt aga cta gtt gtg gac aac ttc ttg ttg aaa tgg tgg gaa aat gtc          856
Phe Arg Leu Val Val Asp Asn Phe Leu Leu Lys Trp Trp Glu Asn Val
                205                 210                 215 gaa aat ggg aca ctc aag gaa gca gtt gac atg aaa acg att cac aag          904
Glu Asn Gly Thr Leu Lys Glu Ala Val Asp Met Lys Thr Ile His Lys
            220                 225                 230 ttg agt    tgagataaat atctatacag aatcaaattt gattgtggca tcacctgtag        960
Leu Ser ctttattatt tgaataaatt tggtaatgtc agttgtaaac gagttagcct ttctttgctg       1020
ttgtggctgt tagcctggtc caaagttaca ttaaattttt tgatgtttcc tgaaagcagc       1080
tgggcagttc tgatattgta acttagattt ggctcccatc atttaaaact gaataaggag       1140
attttcactt cctttatatc cttaaattgg aggaattttt ttgtctcccc ttgttgagat       1200
cttttttcgg ggtgaggaca ttgttatttg ttttgttatg aatcaagtga gactggctat       1260
tcaagcaaaa aaaaaaaaaa aaaaaaa                                           1288

<210> SEQ ID NO 2
<211> LENGTH: 234
<212> TYPE: PRT
<213> ORGANISM: IPIHb (IPP isomerase from Hevea brasiliensis)

<400> SEQUENCE: 2

Met Gly Glu Ala Pro Asp Val Gly Met Asp Ala Val Gln Lys Arg Leu
  1               5                  10                  15
```

-continued

```
Met Phe Asp Asp Glu Cys Ile Leu Val Asp Glu Asn Asp Gly Val Val
            20                  25                  30

Gly His Ala Ser Lys Tyr Asn Cys His Leu Trp Glu Asn Ile Leu Lys
            35                  40                  45

Gly Asn Ala Leu His Arg Ala Phe Ser Val Phe Leu Phe Asn Ser Lys
        50                  55                  60

Tyr Glu Leu Leu Leu Gln Gln Arg Ser Gly Thr Lys Val Thr Phe Pro
65                      70                  75                  80

Leu Val Trp Thr Asn Thr Cys Cys Ser His Pro Leu Tyr Arg Glu Ser
                85                  90                  95

Glu Leu Ile Asp Glu Asp Ala Leu Gly Val Arg Asn Ala Ala Gln Arg
            100                 105                 110

Lys Leu Phe Asp Glu Leu Gly Ile Pro Ala Glu Asp Val Pro Val Asp
            115                 120                 125

Gln Phe Thr Pro Leu Gly Arg Ile Leu Tyr Lys Ala Ser Ser Asp Gly
        130                 135                 140

Lys Trp Gly Glu His Glu Leu Asp Tyr Leu Leu Phe Ile Val Arg Asp
145                 150                 155                 160

Val Asn Val Asn Pro Asn Pro Asp Glu Val Ala Asp Val Lys Tyr Val
                165                 170                 175

Asn Arg Asp Gln Leu Lys Glu Leu Leu Arg Lys Ala Asp Ser Gly Glu
            180                 185                 190

Glu Gly Ile Asn Leu Ser Pro Trp Phe Arg Leu Val Val Asp Asn Phe
            195                 200                 205

Leu Leu Lys Trp Trp Glu Asn Val Glu Asn Gly Thr Leu Lys Glu Ala
        210                 215                 220

Val Asp Met Lys Thr Ile His Lys Leu Ser
225                 230
```

ISOPENTENYL DIPHOSPHATE ISOMERASE FROM *HEVEA BRASILIENSIS* AND RUBBER PRODUCING METHOD USING THE SAME

BACKGROUND OF INVENTION

1. Field of the Invention

The present invention relates to a isopentenyl diphosphate isomerase from *Hevea Brasiliensis* and a rubber producing method using the same.

2. Description of the Prior Art

The isoprenoid biosynthetic pathway is ubiquitous to all living organisms and produces more than 23,000 compounds which play vital roles in the structure of cells, electron transport, photosynthesis, cell-to-cell signaling, and interactions between organisms (Ramos-Valdivia et al., 1997). Several important classes of compounds derived from this complex pathway include sterols, carotenoids, dolichols, ubiquinones, and prenylated proteins (Hahn and Poulter, 1995). All of these compounds are derived from the same building block, IPP. In most eukaryotes, IPP is synthesized from three molecules of acetyl-CoA via the mevalonic acid pathway(Chappell, 1995). Recently, a separate mevalonate-independent pathway was discovered in bacteria and plant(Lichtenthaler et al., 1997; Romer et al., 1993). This pathway utilizes three-carbon precursors such as glyceraldehyde phosphate, pyruvate, and dihydroxyacetone phosphate. The enzyme IPP isomerase (hereafter "IPI") catalyzes the interconversion of IPP to its highly electrophilic isomer, dimethylallyl diphosphate (DMAPP). These two isomers serve as substrates for the synthesis of isoprenoid compounds.

Bioengineering of isoprenoid biosynthesis is of keen interest because of the commercial value of plant compounds such as essential oils, pharmaceuticals, rubber, and waxes. Although the interconversion of IPP and DMAPP is catalyzed by the same IPP isomerase, the equilibrium is in favor of DMAPP production(Sun et al., 1998). This isomerization reaction may be a rate-limiting step for isoprenoid biosynthesis. Expression of an exogenous IPI gene enhanced isoprenoid biosynthesis in *E. coli* (Kajiwara et al., 1997). Transgenic tobacco plants transformed with a *H. brasiliensis* HMGCoA reductase over-produced total sterols up to six-times than the control plants did (Schaller et al., 1995).

Natural rubber (cis-1,4-polyisoprene) is an important raw material for many industrial uses. Although rubber is produced in about 2,000 plant species(Backhaus, 1985), *H. brasiliensis* has been the only commercial source of natural rubber mainly due to its abundance in the tree, its quality and the ease of harvesting. Diminishing acreage of rubber plantation coupled with increasing demand has renewed research interests on the study of rubber biosynthesis and the development of an alternative rubber source. The first step in rubber biosynthesis is the isomerization of IPP to DMAPP by IPP isomerase. The successive head-to-tail condensation reactions of the five-carbon intermediates catalyzed by enzyme(s) referred to as rubber transferase (or polymerase) have been assumed to yield rubber. IPP isomerase activity has been found in bottom fraction and C-serum of rubber latex of *H. brasiliensis* (Koyama et al., 1996; Tangpakdee et al., 1997). The presence of a site-directed specific inhibitor of IPP isomerase, 3,4-oxido-3-methyl-1-butyl diphosphate (OMBPP), inhibited incorporation of IPP into rubber in in vitro rubber assay (Cornish, 1993).

IPP isomerase catalyzes the conversion of IPP to DMAPP, which is an essential step in the biosynthesis of all isoprenoids including carotenoids, growth regulators, and natural rubber. The enzyme from a wide variety of organisms has been studied for a review, see (Ramos-Valdivia et al., 1997). In higher plants, IPP isomerase has been purified and characterized from Capsicum chromoplasts(Dogbo and Camara, 1987), *Cinchona robusta* cell suspension (Ramos-Valdivia et al., 1997), *H. brasiliensis* (Koyama et al., 1996). To date relatively few IPP isomerase sequences from higher plants appear in the literature. Full-length genes for higher plant IPP isomerase are known only for Arabidopsis(Campbell et al., 1997) and two flowering plants Clarkia spp.(Blanc et al., 1996; Blanc and Pichersky, 1995). Partial sequence is also available for tobacco (Accession No. Y09634). However, none of the genes has been implicated in rubber biosynthesis.

As the isomerization of IPP to DMAPP is the first step in rubber biosynthesis, it is plausible for IPP isomerase to play a key role in rubber biosynthesis. Although IPP isomerase activity was observed in both bottom and C-serum fractions from Hevea latex (Tangpakdee et al., 1997), neither the protein nor cDNA encoding IPP isomerase has been isolated and studied from Hevea rubber tree.

SUMMARY OF THE INVENTION

Accordingly, it is an object of the present invention to provide a isopentenyl diphosphate isomerase from *Hevea brasiliensis* and a rubber producing method using the same.

The present invention cloned the gene by screening a latex cDNA library using a PCR-generated probe. Despite the presumed-crucial role of the enzyme in rubber biosynthesis, the gene does not seem to be expressed as an abundant transcript in latex, which contains 30–50% (wt/wt) of cis-1,4-polyisoprene (rubber). In a separate study, the present invention have generated 245 expressed sequence tags (ESTs) to study gene expression profile in the latex of *H. brasiliensis* (Han et al., 1999). The gene encoding IPP isomerase was not identified among the ESTs. Furthermore, initial attempts to screen $1\times10^6$ or less plaques of the latex cDNA library failed to produce any hybridizing cDNA clones. After screening of more than $2\times10^6$ plaques only two hybridizing clones were obtained. Since DMAPP is the primer for the isoprenoid biosynthesis and must be present in any cell compartment where isoprenoids are biosynthesized, the low transcript level of IPIHb gene in the latex is unexpected.

BRIEF DESCRIPTION OF THE DRAWINGS

Other objects and aspects of the present invention will become apparent from the following description of embodiments with reference to the accompanying drawings in which.

DESCRIPTION OF THE PREFERRED EMBODIMENTS

Gene Isolation

Based on the cDNA sequence of *A. thaliana* (Campbell et al., 1997), a PCR primer (downstream) was constructed and used with M13 reverse primer (upstream) to amplify the Hievea IPP isomerase gene using a latex cDNA library of *H. brasiliensis*. The PCR amplified a partial sequence of IPP isomerase coding region. In an attempt to clone the gene by PCR, two PCR primers (IPP-L1 and IPP-L2) from the sequence information were designed and used in combination with vector (M13 forward and reverse) primers. The PCR reaction with the combination of IPP-L2 (downstream) and M13 reverse (upstream) primers yielded about 700-bp fragment. However, no amplification product was obtained with IPP-L1 (upstream) and M13 forward (downstream) primers. The 700-bp PCR fragment showed high sequence identity to the cDNA sequence of *A. thaliana* and was used as a probe to screen the same cDNA library. A total of 2×10$^6$ plaques were screened. The plaques hybridized to the probe and were subjected for in vivo excision. The resulting phagemids contained a full-length cDNA and the gene was designated IPIHb. The DNA sequence is 1,288 bp and has a continuous open reading frame (ORF) encoding a peptide of 234 amino acids with a predicted molecular mass of 26.7 kDa (Sequence ID No. 1). The deduced protein is acidic with an isoelectric point of 4.7 which is lower than that of IPP isomerase from *A. thaliana* (pI=6.0).

Southern Analysis Indicates Two Genes for IPP Isomerase

Figure 1:
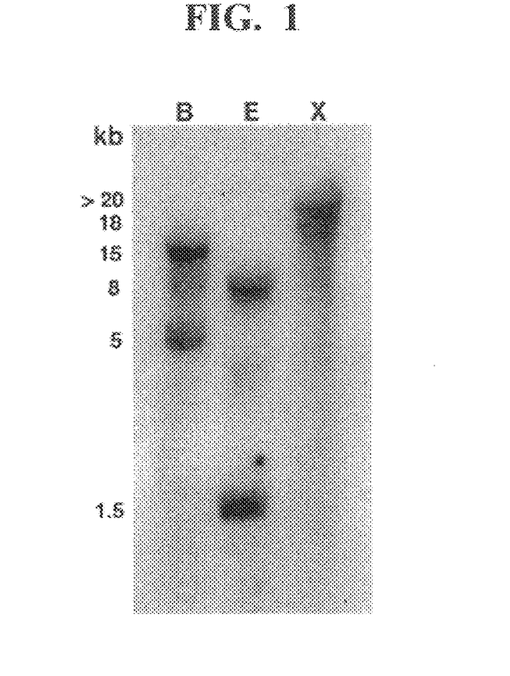
FIG. 1. is Southern blots of genomic DNA from leaves of *H. brasiliensis* probed with internal fragment of IPIHb. Lanes B, E, and X correspond to digestion of total DNA with BamHI, EcoRI, and XhoI, respectively.

To determine the copy number of IPP isonierase gene, Southern blot hybridization analysis was performed using the 700-bp PCR amplified fragment of IPIHb as a hybridization probe. The genomic DNA was digested with BamHI, EcoRI, and XhoI. These enzymes do not have restriction sites inside the coding region of IPIHb. Two hybridizing bands were observed from each restriction digest under both low (55° C.) and high (65° C.) stringency conditions (FIG. 1). These results suggest that IPP isomerase is encoded by multiple genes in Hevea rubber tree. This seems to corroborate the observations in the literature. Campbell et al. (Campbell et al., 1997) reported two cDNA clones encoding IPP isomerase and concluded that the two genes are derived from a small gene family. Multiple isoforms of IPP isomerase have been described in *C. breweri* (Blanc et al., 1996) and *C. robusta* (Ramos-Valdivia et al., 1997). Thus, the occurrence of IPI isoforms is a general feature of higher plants, although specific role of individual isoform is unknown. The presence of uninterrupted 71-amino acid stretch in the region immediately upstream of the ORF of IPIHb suggests that there are isoform(s) targeted to subcellular organelles.

Expression of mRNA for IPIHb

Figure 2:
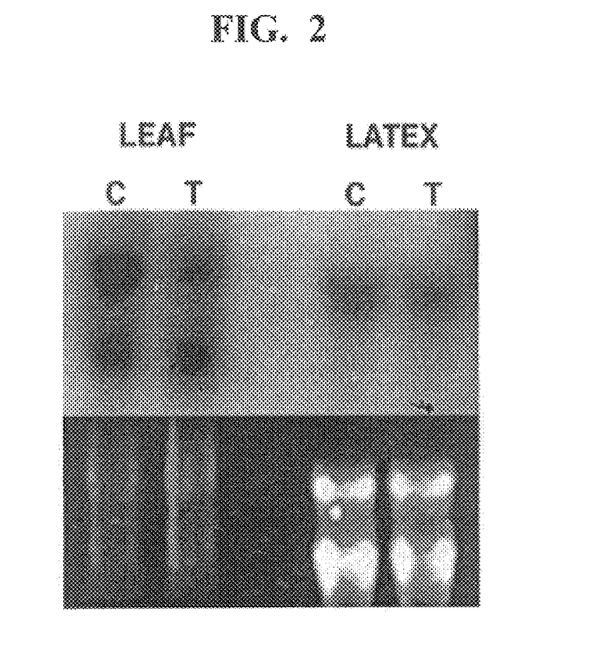
FIG. 2. is Nothern blot analysis of IPIHb transcript. Total RNA isolated from leaf and latex of *H. brasiliensis* were hybridized with a $^{32}$P-labelled internal fragment of IPIHb cDNA. The lower panel shows the ethidium bromide-stained rRNA under UV light before blotting, indicating the loading of similar amount of total RNA. Lanes C and T correspond to untreated control and wounded samples, respectively. For the effect of wounding, five *H. brasiliensis* (clone RRIM600) trees were wounded with six nails above and along the slope of the tapping cut while another five control trees were not punctured. Latex and leaf samples were collected from each tree about 16 h after puncturing.

In the present invention, the expression of the IPP isomerase gene in latex and leaf tissues was investigated. Two different sizes of transcripts (1.2 and 0.6 kb) were hybridized to the probe in the blot containing total RNA from leaf tissues, while only one hybridizing band (1.0 kb) was detected in the blot from latex (FIG. 2). To test the inducible nature of IPP isomerase with wound treatment, leaf and latex samples from wound-treated Hevea trees were obtained(Oh et al., 1999). Analyses of RNA extracted from extruded latex and leaf tissues of the wounded trees showed that the wounding did not change the expression level of IPP isomerase (FIG. 2).

Functional Analysis of IPP Isomerase Expressed in *E. coli*

To further characterize the cloned cDNA encoding Hevea IPP isomerase, a GST-IPIHb fusion gene to produce pGEX-IPIHb was constructed. The pGEX expression system provides simple purification of fusion proteins from crude bacterial lysates. Expression and purification of the GST-IPIHb fusion protein was monitored by SDS-PAGE (data not shown). Enzymatic activity of IPP isomerase was analyzed using either the crude cell extract or the purified GST-IPIHb fusion protein. As a control, either the same bacterial extracts but without IPTG induction or the culture of *E. coli* harboring pGEX that carries a cDNA coding only the GST protein was used.

Figure 3:
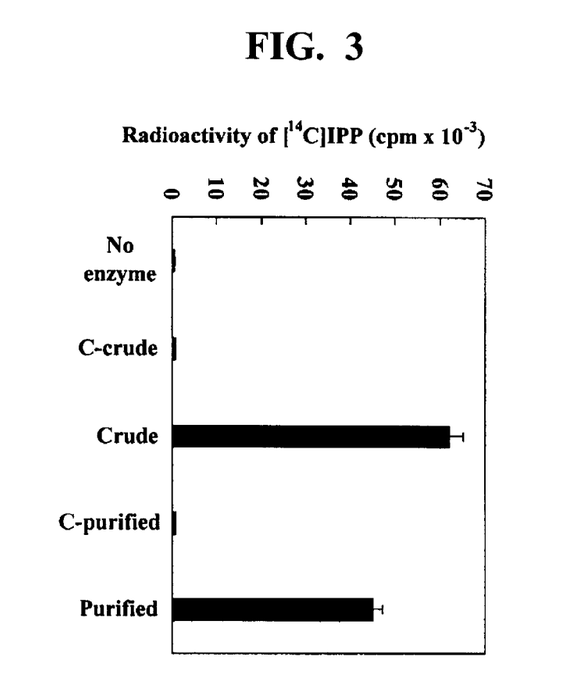
FIG. 3. is Analysis of IPP isomerase activity. IPP isomerase assay was performed in 50 μL of reaction mixture containing 20 μM [$^{14}$C]IPP and 5 μL of enzyme preparation, and radioactivity of the acid labile products was measured by a liquid scintillation counter. Each value is the mean of three experiments; No enzyme, without cell culture extracts; C-crude, bacterial extracts of the cells expressing GST-IPIHb fusion protein without IPTG induction; Crude, cell culture extracts with IPTG induction; C-purified, purified GST-IPIHb fusion protein from the cells without IPTG induction; Purified, purified GST-IPIHb fusion protein from the cells with IPTG induction.
Figure 4A:
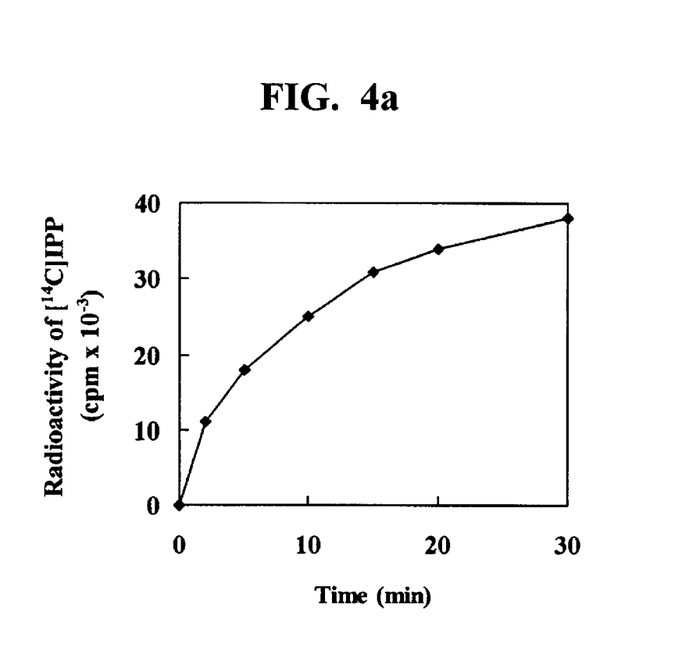
FIG. 4a is Time course and FIG. 4b is concentration dependence of enzymatic activity of IPP isomerase. The IPP isomerase assay was performed in 50 μL of reaction mixture containing 5 μL of purified GST-IPIHb fusion protein for time course experiment, and the reaction was for 10 min with different amounts of enzyme.
Figure 4B:
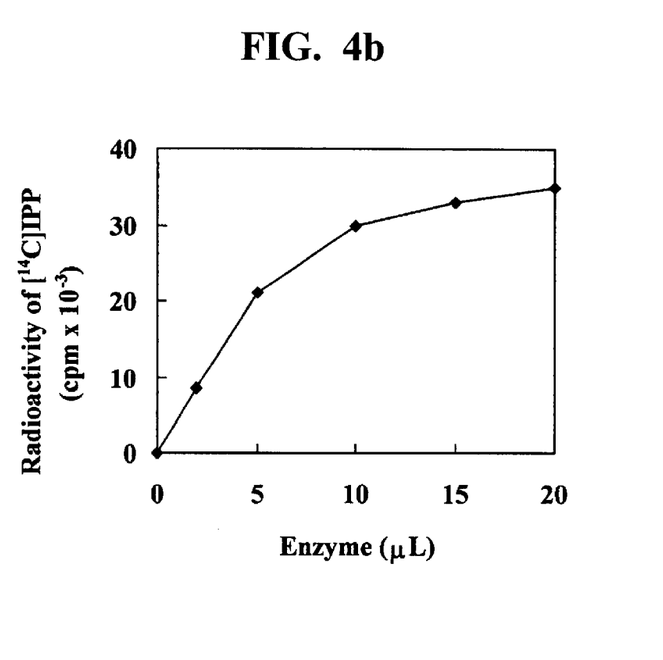

The conversion of IPP to DMAPP was confirmed by the increase in radioactivity resulting from acid labile allylic diphosphate in the reaction mixture. As shown in FIG. 3, basal level of radioactivity was observed for the reaction mixture without enzyme preparation. Similar basal level of radioactivity was detected for the reaction mixture containing enzyme preparation of the cells without IPTG induction. In contrast, a remarked increase in radioactivity was observed for the reaction mixture containing either the crude extract or the purified GST-IPIHb fusion protein of the cells with IPTG induction. In a time course experiment using purified GST-IPIHb fusion protein, it was clearly noted that radioactivity from acid-labile $^{14}$C allylic diphosphate increased with incubation time (FIG. 4a). It was also observed that the radioactivity increased with the amount of purified GST-IPIHb fusion protein added in the reaction mixture (FIG. 4b). The time and concentration dependent increases in radioactivity resulting from acid-labile $^4$C allylic diphosphate indicate that the conversion of IPP to DMAPP occurred in vitro by GST-IPIHb fusion protein. These results reveal that cDNA clone of the present invention encodes a functional IPP isomerase as part of GST-IPIHb fusion protein.

IPP Isomerase is Required for Rubber Biosynthesis In Vitro

Figure 5:
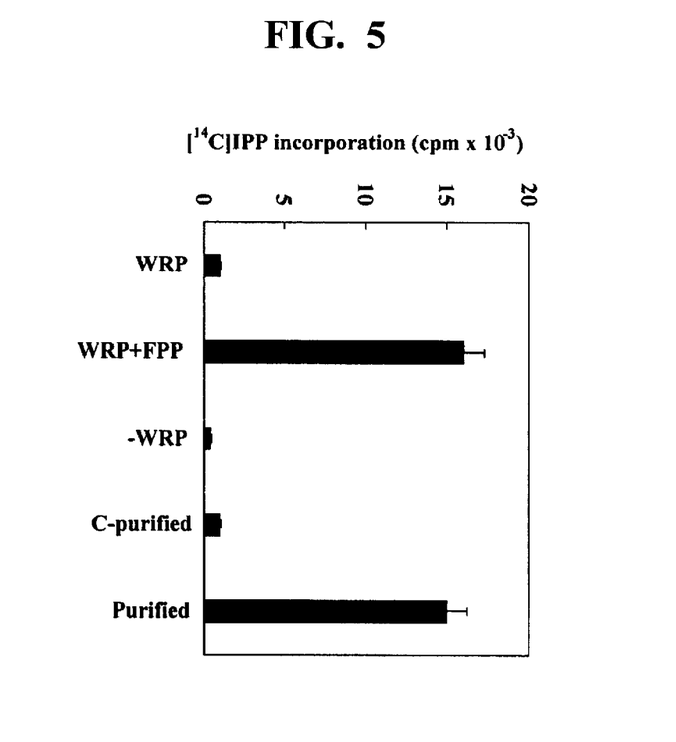
FIG. 5. is Effect of IPP isomerase on rubber biosynthesis in vitro. Incorporation of [$^{14}$C]IPP into growing rubber chain was measured in 50 μL of reaction mixture containing 10 mg of WRP and 5 μL of indicated enzyme preparation, and without FPP, an efficient initiating molecule for rubber biosynthesis. Each value is the mean of three experiments; WRP, rubber assay with WRP alone; WRP+FPP, assay with WRP and FPP; -WRP, assay with purified GST-IPIHb fusion protein and without WRP; C-purified, assay with WRP and purified GST-IPIHb fusion protein from the cells without IPTG induction; Purified, assay with WRP and purified GST-IPIHb fusion protein from the cells with IPTG induction.

Formation of new rubber chain occurs via condensation of IPP to initiating molecules such as GGPP, FPP, GPP and DMAPP. Therefore, general procedure for analyzing rubber biosynthetic activity in vitro contains one of the initiating allylic diphosphates in the reaction mixture. In order to test the role of IPP isomerase on rubber biosynthesis, and confirm further that the cDNA which isolated in the present invention encodes a functional IPP isomerase, in vitro rubber biosynthesis assays using WRP deprived of initiating allylic diphosphates were performed with the addition of IPP isomerase in the reaction mixture. It was clearly noted that FPP, an efficient initiating molecule, was required for rubber biosynthesis in the reaction mixture containing WRP (FIG. 5). The reaction mixture containing bacterial extracts of the un-induced *E. coli* cells harboring same cDNA clone for GST-IPIHb fusion protein showed a basal level of [$^{14}$C]IPP incorporation. In contrast, a marked increase of [$^{14}$C]IPP incorporation into rubber was observed for the reaction mixture containing WRP and purified GST-IPIHb fusion protein (FIG. 5). No incorporation of [$^{14}$C]IPP into rubber was observed in the reaction mixture without WRP, indicating that the increase of radioactivity in the reaction mixture containing WRP and GST-IPIHb fusion protein arose from the synthesis of new rubber chain. These results reveal that the GST-IPIHb fusion protein encoded from cDNA clone of the present invention is catalytically active in converting IPP to DMAPP, a key activation step of the basic five-carbon isoprene unit in rubber biosynthesis.

In the present invention, a DNA sequence that is capable of encoding a IPP isomerase (hereafter "IPIHb DNA sequence") is isolated and a hybrid vector and a transformed host, respectively, that contain the IPIHb DNA sequence are provided.

Within the context of the present invention, a "IPIHb" refers to the IPP isomerase isolated from *Hevea brasiliensis*. A "hybrid vector" as used herein, refers to a vector formed by ligation of DNA from a plasmid, bacteriophage, plant virus or other vectors with DNA or cDNA from Hevea or other organisms that are capable of producing IPIHb, such plants or other organisms being collectively referred to herein as "plant materials."

In one embodiment of the present invention, plant materials from, e.g., Hevea, are used to produce a cDNA. A cDNA library is constructed that is based upon mRNA sequences isolated from total RNA from the plant materials. A first strand cDNA can be synthesized enzymatically using the isolated mRNA as a template, an oligo dT sequence as a primer and a reverse transcriptase as the enzyme. After construction of the first strand cDNA, a second strand cDNA can be synthesized enzymatically using the first strand cDNA as a template and a DNA polymerase as the enzyme. The resulting double-stranded cDNA molecules are inserted into a suitable vector, to produce a cDNA library.

The resulting cDNA library may be screened for the full-length sequence of IPIHb gene using a nucleic acid probe specific for the IPIHb gene (hereafter "IPIHb gene specific probe"). The IPIHb gene-containing cell can then be propagated and large amounts of DNA sequence encoding IPIHb can be extracted.

In a preferred embodiment of the present invention, a nucleic acid probe for the identification of IPIHb gene is produced by PCR amplification of the cDNA library using IPP isomerase specific primers.

Plant cDNA or cDNA from other organisms that hybridizes with a labelled nucleic acid probe specific for the IPIHb gene can be identified and isolated. The isolated DNA can be ligated to a vector DNA to produce a hybrid vector. The hybrid vector can be used to transform a competent host and to induce the production of IPP isomerase in the host.

A vector that is suitable for use in the context of the present invention can be a plasmid or a virus that is capable of being transferred into a host cell or of infecting a host cell and of replicating in a host cell. In a preferred embodiment, a suitable vector is one that is capable of carrying as an insert an entire IPIHb DNA sequence in a non-essential region of the vector DNA.

A suitable transformed host is one that is capable of expressing the IPIHb DNA sequence. In a preferred embodiment, a suitable transformed host is incapable of catalyzing the conversion of IPP to rubber. Such a host maybe a plant, a bacterium or a fungus. The plant host may be an annual plant such as tobacco species, a grass species or a perennial plant species. The bacterium can be any bacterium, e.g., *E. coli,* a Bacillus species or an Agrobacterium species. The fungus is selected from the group consisting of a lactarius species and an Aspergillus species.

In another embodiment of the present invention, the DNA fragment that contains the IPIHb gene can be ligated to a suitable promoter so as to place the gene under the control of the promoter. A suitable promoter is one that is capable of functioning in a transformed host. For example, if the host to be transformed is a plant, the IPIHb gene can be ligated to a plant promoter such as Pnos, the promoter for nopaline synthetase; if the host to be transformed is a bacterium, the IPIHb gene can be ligated to a bacterial promoter such as the trp or tac promoter of *E. coli.* In the alternative, the IPIHb gene can be ligated to a virus promoter such as the 16S and 35S promoter of cauliflower mosaic virus.

In a preferred embodiment of the present invention, a cDNA library, instead of a genomic DNA library, is constructed using mRNA isolated from total RNA. Total RNA is obtained from plant materials by a method that is substantially the same as that of Kush et al. Proc Natl Acad Sci USA 87, 1787–1790 (1990), the contents of which is incorporated herein by reference. The plant materials that are used for the isolation of mRNA can be from any plant or organisms that are capable of synthesizing rubber. For example, since Hevea trees produce rubber from latex, mRNA capable of encoding IPIHb can be obtained from Hevea latex.

The isolation of mRNA herein capitalizes on the presence of a poly(A) tail at the 3' end of the mRNA. The 3' tail is utilized to separate the mRNA from the other RNA species. Separation is achieved by chromatography on an oligo(dT) cellulose column by binding of the poly(A) tail of mRNA with the T residues on the cellulose column. The unbound RNA can be washed free of the column and the mRNA can be eluted by buffers that destabilize the A-T duplex. The RNA concentration is then determined spectrophotometrically. The isolated mRNA is then used as a template for synthesis of first-strand cDNA molecules. The first-strand cDNA is, in turn, used as a template in a second-strand DNA synthesis utilizing, e.g., according to Sambrook et al., MOLECULAR CLONING, Cold Spring harbor, N.Y. 1987, the contents of which are incorporated herein by reference.

A suitable vector capable of carrying an entire gene in a non-essential region of its DNA and capable of replicating in a host cell, e.g., a lambda vector, can be ligated to the DNA fragments to generate a library of recombinant DNA molecules. In vitro packaging of these recombinant molecules can yield an infectious phage stock consisting of recombinant clones. The recombinant DNA libraries constructed in this manner can be used for isolation of the IPIHb gene and other genes that are important in the biosynthesis of rubber utilizing either nucleic acid probes or antibodies if the cDNA library expresses the cDNA.

A nucleic acid probe for the detection of the IPIHb gene can be modified to detect extremely small amounts of the gene, e.g., by labeling the probe with [$^{32}$P]-phosphate at the 3' or 5' end, or with biotin moieties by conventional laboratory techniques as in, e.g., according to Sambrook et al., MOLECULAR CLONING, Cold Spring Harbor, N.Y. 1987, the contents of each of which are incorporated herein by reference. The radioactive labeling can be performed using commercially available 3' or 5' end labeling kits from, e.g., Amersham Corporation (Arlington Heights, Ill.) or New England Nuclear (Boston, Mass.), and following the manufacturer's directions. The IPIHb gene in the DNA libraries can then be identified by hybridization with the labeled probe.

In another embodiment of the present invention, a recombinant lambda Phage containing Hevea cDNA library is screened substantially according to the method of Sambrook et al., loc. cit., using [$^{32}$P]-labelled IPIHb specific oligonucleotide.

The clone that carries the IPIHb gene and that reacts positively with the IPIHb gene specific probe can be isolated and converted into a plasmid by in vivo excision according to the protocol provided by the cDNA library kit. This method of conversion of phage DNA into plasmid is feasible because when the Hevea cDNA library is constructed into the Uni-ZAP II vector (Stratagene, La Jolla, Calif.) that was designed for such in vivo excision. The plasmid is transferred and maintained in E. coli for production of large quantities of this gene. The E. coli cells containing the plasmid with the IPIHb qene are propagated to produce large quantities of the IPIHb DNA sequence. This DNA can be extracted from the transformed hosts in accordance with conventional laboratory techniques.

The present invention relates to DNA sequences and recombinant DNA molecules coding for the Hevea small rubber particle protein (IPIHb) and processes for the production of recombinant protein, to vectors containing the sequences, to cultures producing recombinant protein, and to the materials significant in the production of recombinant protein. A DNA sequence encoding IPIHb or a protein having substantially the same biological activity for rubber biosynthesis as IPIHb is shown.

The isolated recombinant vector containing cDNA encoding the IPIHb is transferable to other prokaryotic or eukaryotic host organisms wherein the IPIHb DNA will be expressed to produce functional IPIHb for rubber biosynthesis.

The following example is given by way of illustration to facilitate a better understanding of the present invention and are not intended to limit the scope thereof.

EXAMPLE 1

Plant Materials

Latex and leaf samples were obtained from mature rubber plants (H. brasiliensis clone RRIM600) growing at the Rubber Research Institute of Malaysia, Selangor, Malaysia. Latex exuding from the tapped trees was collected while continuously mixing it with an equal volume of 2×RNA extraction buffer (0.1 M Tris.HCl, 0.3 M LiCl, 0.01 M EDTA, 10% SDS, pH 9.5) either at ambient temperature or on ice(Han et al., 1999). The collected samples were frozen in liquid nitrogen and shipped back to the laboratory on dry ice.

Total and Poly(A)$^+$RNA Isolation

RNA extraction from latex was performed as described previously(Oh et al., 1999) using the Qiagen Rneasy Plant Minikit (Qiagen Inc, Chatsworth, Calif.) Poly(A)$^+$RNA was isolated using Oligotex-dT™ mRNA kit (Qiagen Inc, Chatsworth, Calif.).

PCR Amplification of H. brasiliensis IPP Isomerase (IPIHb)

PCR amplification was preformed using latex cDNA library as a template. A PCR primer (IPP-A2) corresponding to the sequences from +606 to +629 bp in Arabicopsis IPP isomerase was designed. The primers used to amplify a fragment of the IPIHb cDNA were IPP-A2 (5'-GTAATCAAGTTCATGCTCTCCCCA-3') and M13 reverse primer. PCR was performed for 30 cycles of 30 s at 94° C., 30s at 55° C., and 30 s at 72° C., with a 5-min pre-heat and a 7-min final extension at 72° C. The PCR product was excised from an agarose gel and purified with the QIAEX II Agarose Gel Extraction Kit (QIAGEN, Hilden, Germany). Purified PCR products were ligated into the pGEM®-T vector (Promega, Madison, Wis.). Plasmids were transformed into E. coli strain XL1-Blue, isolated, and sequenced. Based on the PCR-amplified sequence of Hevea IPP isomerase, two primers were designed, IPP-L1 as downstream primer (5'-TATGAGCTACTCCTTCAGCAACGCTCT-3') and IPP-L2 as downstream primer (5'-ATCAAGTTCATGCTCTCCCCACTTTCC-3'). The IPP-L1 and L2 primers were used with M13 forward and reverse primers, respectively.

Construction and Screening of Latex cDNA Library

A cDNA library was constructed in a Uni-ZAP II vector according to the supplier's instructions (Stratagene, La Jolla, Calif.) using poly(A)$^+$RNA prepared from latex as described above. The primer (IPP-L2, downstream) and M13 reverse primer (upstream) were used to amplify partial IPP isomerase fragment from the latex cDNA library. The 700-bp PCR product was used to screen 2×10$^6$ plaques of the latex cDNA library as described previously(Oh et al., 1999). The cDNA clones hybridized to the probe were subjected to in vivo excision according to the protocol provided by the cDNA library kit and sequenced. A clone carrying a full-length cDNA insert was isolated and designated as IPIHb.

Sequencing of cDNA Clones and Computer Analysis

Plasmid DNA for sequencing reactions was prepared by the alkaline lysis method (Sambrook et al., 1989) using Wizard® Plus SV Minipreps DNA Purification System kit (Promega, Madison, Wis.). The sequencing reaction was performed with the ALF Express AutoRead Sequencing kit (Pharmacia Biotech, Uppsala, Sweden) using the fluorescent dye-labeled M13 forward or reverse primer (provided by the kit). The nucleotide sequences were obtained by electrophoresis on an ALF automatic sequencer (Perkin Elmer Co.).

EXAMPLE 2

Wounding Treatment

Latex and leaf samples were collected from the rubber trees wounded with six nails above and along the slope of the tapping cut(Oh et al., 1999).

Southern and Northern Blot Analysis

Genomic DNA from leaf tissues of a mature H. brasiliensis RRIM600 was prepared as described(Oh et al., 1999). Genomic DNA (8–10 μg) was digested with the indicated restriction enzymes, size-fractionated by electrophoresis in 0.8% (w/v) agarose gels, blotted, and cross-linked to Hybond-N nylon membrane (Amersham Life Science, Little Chalfont, England)) by UV radiation. For northern blot, twenty micrograms of total RNA were electrophoresed on a 1.2% agarose-formaldehyde gel, transferred, and crossed-linked as for Southern blot. The probe for both hybridizations was a $^{32}$P-labelled 700-bp PCR generated fragment (described above) of IPIHb cDNA. Hybridization was for 18 h at 55° C. for northern and 65° C. for Southern in 0.9 M sodium chloride, 50 mM sodium phosphate (pH 7.6), 5 mM EDTA, 0.4% (w/v) SDS, 5×Denhardt's solution, and 200 μg salmon sperm DNA. The blot was washed at either 55° C. for low stringency or 65° C. for high stringency twice in 0.5×SSPE, 0.1% SDS, and twice in 0.1×SSPE, 0.1% SDS. The membrane was exposed to an X-ray film overnight at −70° C.

EXAMPLE 3

Heterologous Expression of IPIHb Protein in *E. coli*

The IPIHb gene was cloned in the EcoRI-XhoI site of pGEX (an IPTG-inducible expression vector; Pharmarcia Biotech, Uppsala, Sweden) to construct pGEX-IPIHb. The *E. coli* XL1-Blue transformed with pGEX-IPIHb was grown to mid-stationary phase in Luria Broth (LB) containing 50 mg/l ampicillin at 30° C. with vigorous aeration. The cultures were induced by adding IPTG to a concentration of 0.1 mM and then incubated for another 6 h. All subsequent steps were carried out at 4° C. The cells were harvested, washed with 0.1 M potassium phosphate (pH 7.4) by centrifugation (5000×g, 10 min), and then disrupted by sonication. The sonication was carried out for six cycles of 30 s bursts followed by 30 s intervals in 1 ml of buffer containing 0.1 M potassium phosphate (pH 7.4). The homogenate was centrifuged at 10,000×g for 10 min and the supernatant was subjected to SDS-PAGE with 12.5% slab gels according to the standard method of Laemmli(Laemmli, 1970). Proteins were stained by Coomassie Brilliant Blue R-250. The fusion protein was affinity purified using Glutathione Sepharose 4B affinity matrix (Pharmarcia Biotech, Uppsala, Sweden) according to the instructions of manufacturer.

Assay of IPP Isomerase Activity

The assay is based on the acid lability of the allylic diphosphate described by Satterwhite(Satterwhite, 1985). The incubation mixture, total volume 50 μl, contained 100 mM Tris-HCl, pH 7.5, 1.5 mM $MgCl_2$, 1.5 mM $MnCl_2$, 2 mM DTT, 25 mM KF, 20μM [$^{14}$C]IPP (55 mCi mmol$^{-1}$, Amersham), and suitable amounts of enzyme preparation. After 10 min incubation at 30° C., 200 μL methanol:HCl (4:1, v/v) and 0.1 μL water were added and incubation was continued for 15 min at 37° C. The allylic products were extracted with 2×200 ml toluene. The combined extracts were mixed with 4 ml Ready Solv HP scintillation cocktail (Beckman), and the radioactivity was determined using an LS 6500 liquid scintillation counter (Beckman).

In Vitro Rubber Biosynthesis Assay

Washed rubber particles (WRP) were prepared by repeated centrifugation/flotation procedure as described (Cornish and Backhaus, 1990; Siler and Cornish, 1993). Rubber biosynthetic activity iii vitro of the reaction mixtures was determined by the methods previously described (Cornish and Backhaus, 1990; Siler and Cornish, 1993). WRP was incubated in 50 μl of reaction mixture containing 100 mM Tris-HCl, pH 7.5, 80 μM [$^{14}$C]IPP (55 mCi mmol$^{-1}$, Amersham), 20 μM FPP, 1 mM $MgSO_4$ and 1 mM DTT for 6 h at 25° C. To investigate the role of IPP isomerase on rubber biosynthesis, FPP, an efficient initiating molecule for rubber biosynthesis, was removed from the reaction mixture, and, instead, suitable amounts of IPP isomerase were added to convert IPP to DMAPP that is one of the initiating molecules for rubber biosynthesis. For control experiment, 25 mM of EDTA was added to the reaction mixture to chelate $Mg^{2+}$ion necessary for rubber transferase activity. The resulting [$^{14}$C]IPP-incorporated rubber was quantified by using either a filtration or a benzene extraction method. For filtration method, the reaction mixture was filtered through either 0.02 or 0.1 μm anodise membrane (Whatman), the filter was subjected to repeated washing with 1 M HCl and 95% ethanol(Cornish and Backhaus, 1990), and the remaining-radioactivity on the washed filters was determined by a liquid scintillation counter (Beckman). For benzene extraction method, the reaction mixture was extracted three times with two volumes of benzene, the benzene extract was mixed with a Ready Solv HP scintillation cocktail (Beckman), and the radioactivity was determined by a liquid scintillation counter.

What is claimed is:

1. An isolated nucleic acid molecule encoding a Hevea IPP isomerase having an amino acid sequence as depicted in Sequence ID No.: 2.

2. An isolated nucleic acid molecule having a nucleic acid sequence as depicted in Sequence ID No.: 1.

3. A vector comprising the nucleic acid molecule of claim 1.

4. A vector comprising the nucleic acid molecule of claim 2.

5. The vector of claim 3, wherein the nucleic acid molecule encoding the Hevea IPP isomerase is operatively linked to a promoter element.

6. The vector of claim 4, wherein the nucleic acid molecule encoding the Hevea IPP isomerase is operatively linked to a promoter element.

7. The vector according to claim 5, wherein said promoter is selected from the group consisting of a bacterial promoter, a plant promoter and a virus promoter.

8. The vector according to claim 6, wherein said promoter is selected from the group consisting of a bacterial promoter, a plant promoter and a virus promoter.

9. The vector as claimed in claim 3, wherein said vector is capable of being transferred to and replicating in a host.

10. The vector as claimed in claim 4, wherein said vector is capable of being transferred to and replicating in a host.

11. A transformed host comprising the vector as claimed in claim 9, wherein said host is capable of expressing the nucleic acid molecule.

12. A transformed host comprising the vector as claimed in claim 10, wherein said host is capable of expressing the nucleic acid molecule.

13. A transformed host as claimed in claim 11, wherein said host is selected from the group consisting of a plant, bacterium, a yeast and a fungus.

14. A transformed host as claimed in claim 12, wherein said host is selected from the group consisting of a plant, bacterium, a yeast and a fungus.

15. A process for the production of rubber in vitro comprising the steps of providing a nucleic acid molecule as claimed in claim 1, transferring said nucleic acid molecule to a host cell to produce a transformed host cell and culturing said transformed host in a suitable medium for the production of IPIHb, using said IPIHb to catalyze the synthesis of rubber in vitro.

16. A process for the production of rubber in vitro comprising the steps of providing a nucleic acid molecule as claimed in claim 2, transferring said nucleic acid molecule to a host cell to produce a transformed host cell and culturing said transformed host in a suitable medium for the production of IPIHb, using said IPIHb to catalyze the synthesis of rubber in vitro.

17. A process for the production of rubber in vivo comprising the steps of providing a nucleic acid molecule as claimed in claim 1, transferring said nucleic acid molecule to a host cell to produce a transformed host cell and culturing said transformed host in an environment that is suitable for the production of rubber in vivo.

18. A process for the production of rubber in vivo comprising the steps of providing a nucleic acid molecule as claimed in claim 2, transferring said nucleic acid molecule to a host cell to produce a transformed host cell and culturing said transformed host in an environment that is suitable for the production of rubber in vivo.

* * * * *